United States Patent [19]

Williams

[11] Patent Number: 5,388,592
[45] Date of Patent: Feb. 14, 1995

[54] PROTECTIVE BARRIER

[76] Inventor: Tracey Williams, 533 Fourteenth St., San Francisco, Calif. 94103

[21] Appl. No.: 82,983

[22] Filed: Jun. 25, 1993

[51] Int. Cl.$^6$ ............................................. A61F 6/02
[52] U.S. Cl. ................................... 128/842; 128/844
[58] Field of Search ............... 128/842, 844, 918, 857, 128/858; 604/330, 347–353

[56] References Cited

U.S. PATENT DOCUMENTS

| | | | |
|---|---|---|---|
| 1,491,011 | 7/1922 | Hodgin | 128/844 |
| 1,986,988 | 8/1934 | Treadwell | 128/136 |
| 2,276,612 | 8/1941 | Ellis | 128/146 |
| 2,591,783 | 4/1952 | Craddock | 128/132 |
| 2,667,869 | 2/1954 | D'elia | 128/857 |
| 3,536,066 | 11/1970 | Ludwig | 128/132 |
| 4,781,709 | 11/1988 | Grubman | 128/844 |
| 4,815,456 | 3/1989 | Rubin et al. | 128/859 |
| 4,942,885 | 7/1990 | Davis | 128/844 |
| 4,974,605 | 12/1990 | Esqueda | 128/857 |
| 4,993,433 | 2/1991 | Reddy | 128/844 |
| 5,016,649 | 5/1991 | Johnson | 128/859 |
| 5,146,930 | 9/1992 | Richardson | 128/842 |
| 5,209,241 | 5/1993 | Hardy | 128/844 |

FOREIGN PATENT DOCUMENTS

| | | | |
|---|---|---|---|
| 2606275 | 5/1988 | France | 128/918 |
| 2630001 | 10/1989 | France | 128/918 |
| 9013277 | 11/1990 | WIPO | 128/918 |

OTHER PUBLICATIONS

The Eve's Garden Latex Panty, manufactured by Eve's Garden International, Ltd., of New York, N.Y.

*Primary Examiner*—Michael A. Brown
*Attorney, Agent, or Firm*—Michael A. Glenn

[57] ABSTRACT

A disposable protective barrier formed of an elongated planar membrane comprising a strong virus impermeable film prevents the exchange of body fluids during oral sex. In one embodiment, the invention provides a protective mask that shields the facial area of the wearer, including the mouth, side face, the front of the nose, and the front and under chin, from undesirable exposure to infection carrying microorganisms, while permitting unrestricted freedom of movement of the wearer's jaw, lips, nose, and tongue. Another embodiment of the invention provides a brief that uses any of various securing means that may include variable strap size and contoured thigh placement. Materials that exhibit plastic cohesive attraction to human skin are employed to secure the mask or brief to the wearer, thereby ensuring that the garment stays in the desired position for greater protection when in use.

3 Claims, 3 Drawing Sheets

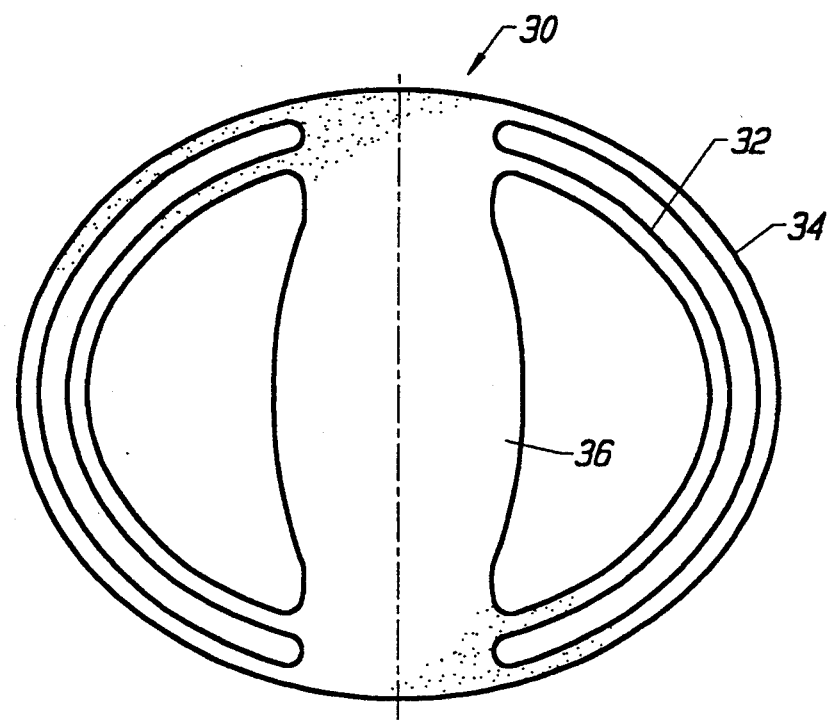
FIG. 3
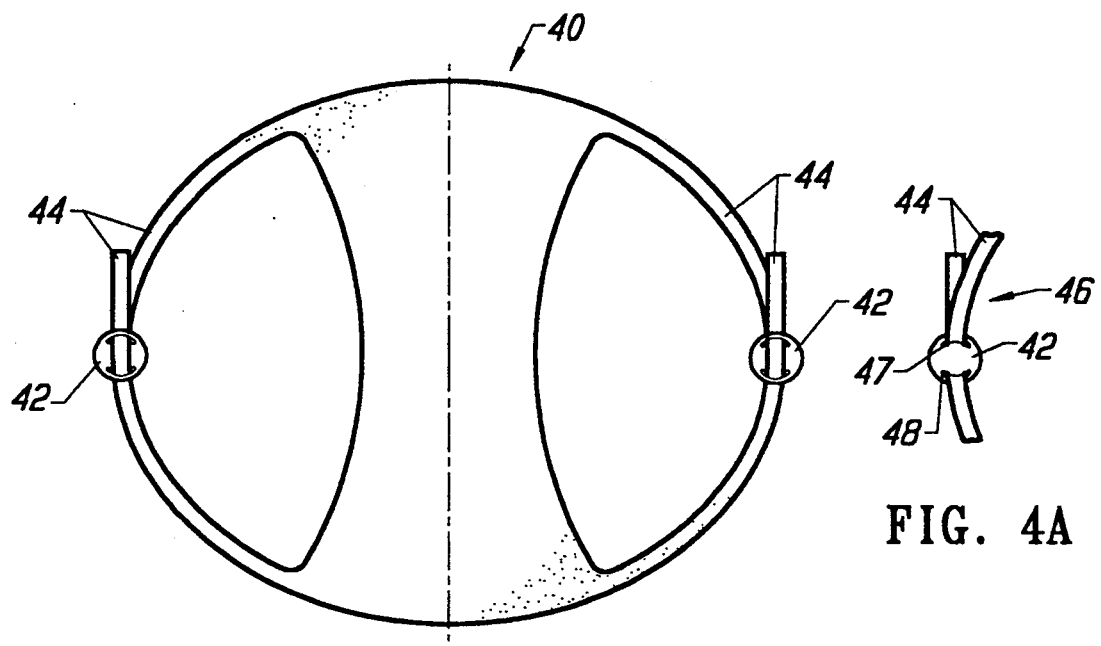
FIG. 4
FIG. 4A

PROTECTIVE BARRIER

BACKGROUND OF THE INVENTION

1. Technical Field

The present invention relates to protective barriers, designed for use during sexual activity. More particularly, the present invention relates to a protective barrier that is useful for protecting a wearer against infection from communicable diseases during sexual activity.

2. Description of the Prior Art

Acquired Immune Deficiency Syndrome ("AIDS") is a particularly deadly communicable disease that has no known cure and that is therefore of substantial concern to all. Although AIDS was initially thought to afflict only intravenous drug users and homosexual men, increasing numbers of heterosexual women and men are exposed to the AIDS virus when they engage in unsafe sexual activities.

One way that AIDS may be spread is when one is exposed to the blood and other body fluids of partners as they engage in consensual sexual activities. Much emphasis has been given to preventative steps designed to lessen the risk of sexual activities, such as oral sex. For example, health educators instruct oral sex practitioners to use sliced condoms, sliced gloves, and kitchen cling wrap as protective barriers against exchanging body fluids during oral sex.

Oral dams, such as are used in dentistry, have been used to provide a barrier against the passage of fluids between partners during sexual activity, but the material is thick and unpleasant in use. Additionally, there is no effective way to secure such material, i.e. it cannot be worn during sexual activity, but must be held in place, thereby providing a significant distraction, and increasing the likelihood that the barrier can slip from place and allow an unwanted exchange of fluids between partners.

The prior art teaches various protective masks and briefs which are provided expressly for the purpose of preventing the transmission of body fluids during oral sex. In practice, known masks and briefs are only of limited effectiveness in preventing the transmission of sexually transmitted diseases, such as the human immune virus which leads to the development of AIDS.

Treadwell, U.S. Pat. No. 1,986,988, teaches a two part applicator for mouth suction which extends over the immediate area of wearer's mouth and provides a membrane and a separate cup which is capable of receiving fluids, such as snake bite poison.

Rubin, U.S. Pat. No. 4,815,456, teaches a one piece membrane similar in general size and configuration to that of Treadwell and having a central protuberant extension of the membrane for participants in oral sex.

Johnson, U.S. Pat. No. 5,016,649, teaches a protective mask having an elongated film that covers the side of the face, mouth, and under chin. A string to fastens the mask to a wearer's face.

The foregoing patents do not teach the need to cover the nasal mucus membrane lining which could absorb opportunistic viruses. Treadwell, Rubin, and Johnson teach a mask that only provides coverage of side of the wearer's face and mouth. Johnson's mask is the only one of the three masks that covers the wearer's under chin.

The above mentioned patents teach the use of either a string or a single set of ear-slots to secure to the mask to the wearer's face. A mask that is secured to a wearer's face with a string rubs against the skin during use, causing skin irritation and/or burning. The use of string also presents the risk that the mask will loosen during use, exposing the partners to an exchange of body fluids.

Masks that are secured to a wearer's face with a single set of ear-slots tend to have a loose fit if the wearer's face is smaller than the length of the mask. Wearers with faces larger than the length of the mask may experience reduced blood flow in the covered areas and restricted motion of the jaw, lips, and tongue. It is also likely that the mask will leave stretch marks on wearer's face after use.

The prior art also teaches the use of protective briefs. For example, the Eve's Garden Latex Panty, manufactured by Eve's Garden International, Ltd., of New York, N.Y. provides a reusable latex barrier having a brief configuration that allows the barrier to be worn during sexual intercourse. The brief is made of a resilient material that yields during sexual activity. However, the brief is not useful as a barrier during oral sex because it is not adjustable and therefore may not always fit properly. That is, it may be too loose and not provide adequate protection; or it may be too tight and may rupture during use. If the brief is too loose, it may need to be knotted to take up any slack; if the brief is too tight, it will not be comfortable to wear. Because the brief is reusable, it tends to stretch out of shape over time after repeated use. Thus, the brief becomes less effective as a barrier with each use.

Ludwig, U.S. Pat. No. 3,536,066, teaches a brief that incorporates birth control protection. Ludwig's invention provides a dual contraceptive appliance that functions as a mechanical barrier between the genitalia, thereby preventing the exchange of body fluids between partners. Ludwig's brief has the shape of a bikini brief with a reversible proboscis to receive a penis when worn by a women during penetration or to contain an erect penis when worn by a man.

The Ludwig teaching is primarily concerned with providing a means of birth control. The reversible proboscis interferes with oral contact between the partners. The Ludwig teaching also relies on the elasticity of the material from which the brief is made to provide a garment that fits all body sizes. Persons who are larger than the maximum expanded elasticity of the brief may break the brief during application or use. Ludwig's invention also may reduce the blood flow of wearer to his or her genitalia, which could lead to decreased sexual sensitivity.

Craddock, U.S. Pat. No. 2,591,783, teaches a shield related to safety or sanitary protecting devices, particularly devices for preventing the spread of venereal diseases. The shield has a centrally disposed opening with straps extended from the shield corners that attach the shield to the wearer's body. The shield also has an annular flange that extends around the opening and that is positioned in a plane parallel to the face of the shield. The Craddock brief was designed for use with a condom during penetration, and therefore does not protect against an exchange of body fluids during cunnilingus because the female genitals are exposed.

Given the risks of contracting venereal diseases by engaging in sexual activity and the dire consequences if such a disease is acquired, it behooves sexual partners to practice safe sex. Although condoms provide a reasonable measure of protection during sexual intercourse, there has heretofore been no reliable device for protecting partners during oral sex.

SUMMARY OF THE INVENTION

The present invention provides a disposable barrier against the exchange of body fluids during oral sex. The preferred embodiment of the invention is an improved protective mask which is capable of protecting the facial area of the wearer, including the mouth, side face, and front and under chin, from undesirable exposure to infection carrying microorganisms. The invention permits unrestricted freedom of movement for the jaw, lips, nose, and tongue of a wearer, while providing a tailored fit formed by the mask shape, the cohesive attraction to human skin of the material from which the mask is formed, and the triple set of ear-slots that secure the mask to the wearer. The invention also shields the front of the wearer's nose while providing side ventilation.

The protective mask is formed of an elongated, planar membrane of a strong virus impermeable film material. The mask may be fabricated from various materials that include plastic or latex having a thickness of from 0.00125 to 0.004 inches and a density sufficient to prevent passage of viral material, preferably smaller than 25 nm. The preferred mask measures 17×6 inches.

The invention provides multiple ear-slots to adjust to many face sizes, reducing possible slippage or potential reduction of blood flow to covered areas. The ear-slots rest comfortably around the wearer's ear. Because the invention provides the wearer with multiple ear-slots rather than a string to secure the mask to the wearer's face, there is less chance of the mask rubbing against the skin during use, and there is less chance of the mask slipping and allowing an exchange of body fluids between the partners.

Another embodiment of the invention provides a brief that uses several forces to secure the brief to the wearer, thereby ensuring that the brief stays in the desired position for greater protection. This embodiment of the invention provides multiple security mechanisms to ensure the wearer's protection in the event that one security mechanism fails. Thus, the brief may be provided with any of various securing means that may include optional strap sizes, contoured thigh placement, and materials that exhibit plastic cohesive attraction to human skin.

BRIEF DESCRIPTION OF THE DRAWINGS

FIG. 3 is a top plan view of a dual brief according to another embodiment of the invention;

FIG. 4 is a top view plan of a cinch adjustable brief according to another embodiment of the invention.

DETAILED DESCRIPTION OF THE INVENTION

The invention provides disposable protective barriers for use during sexual activity. The protective barriers are provided in the form of a garment that is intended to prevent the exchange of fluids between partners during oral sex. The various embodiments of the invention include a mask and a brief. This invention is an especially effective tool for use in the prevention of sexually transmitted diseases ("STDs"), including the human immune virus leads to the development of Acquired Immune Deficiency Syndrome ("AIDS").

Figure 1:
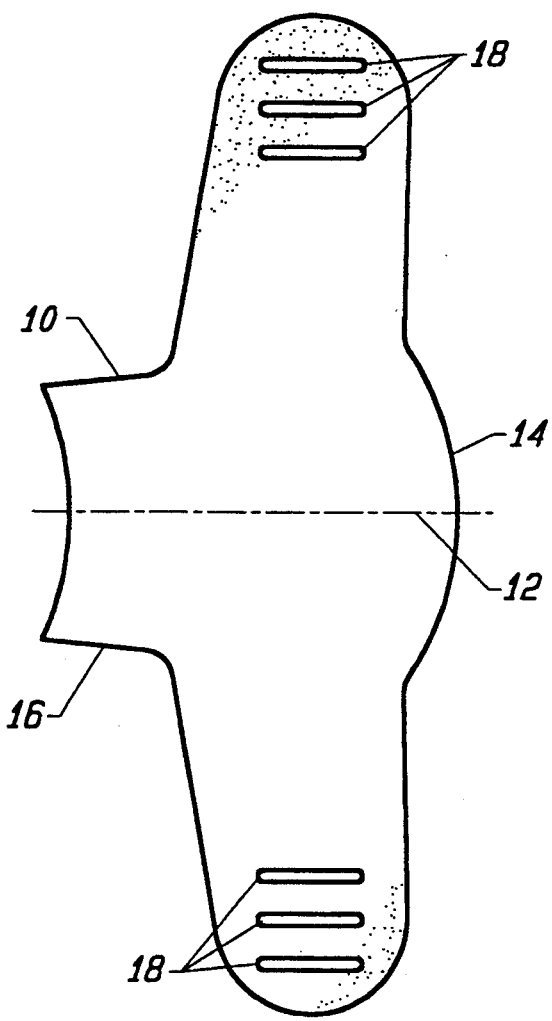
FIG. 1 is a top plan view of a mask according to the preferred embodiment of the invention.

FIG. 1 is a top plan view of a mask according to the preferred embodiment of the invention. The mask 10 is formed by an elongated, planar membrane of durable film material, having, when placed flat, a horizontal axis 12 and an outlined configuration which is symmetrical about that axis. The outlining configuration has a first portion 14 that extends upwardly when the mask is worn to shield the nose; and a second portion 16 that extends downwardly and rearwardly over the chin and mid area between chin and neck of a wearer when worn.

This mask is secured to the wearer's face with the most comfortably and securely fitting of three independent sets of open ear slots 18, depending upon the size of the wearer's head. The mask wraps over the wearer's mid and lower face and conforms to the contour of the wearer's face due to the film's cohesive attraction to human skin. The mask's contoured design permits side ventilation for wearer to inhale and exhale while providing free movement of the wearer's jaw, lips, and tongue.

In the preferred embodiment of the invention, the mask ear slots 18 offer the wearer three securing options for comfort. The mask of the invention is thus tailored to fit wearer's unique facial structure while worn as a hygienic barrier that can cover mid and lower face areas. In addition to ear-slots, the mask material's cohesive attraction to the wearer's skin, as a result of natural moisture on the surface of the skin, causes the mask to fit the contour of the wearer's check bones and upper and lower chin much like a glove fits a hand. The mask is permitted to move simultaneously with the wearer's skin and facial muscles. In other embodiments of the invention fewer or more ear slots may be provided.

The nose shield 14 is shaped to the wearer's nose to provide a barrier against fluids, while also providing an opening for air to allow the wearer to continue inhaling and exhaling in normal fashion while wearing the mask. Tension placed on the mask when the mask to secured to the wearer's face by the ear slots 18 pulls the mask material firmly to the wearer's face, creating an arched cup space near the wearer's nose that provides ventilation to the wearer's nose.

The neck bib 16 provides coverage of the wearer's face area between the chin and the neck line. This protection is most needed when the wearer is reclining horizontally while engaged in oral sex with a partner straddled over the wearer. When the wearer is in this position, the neck bib guides drops of body fluid away from the wearer's face to the lower neck. The neck bib 16 prevents body fluid from sliding from the front of the mask unto the wearer's chin and under the mask.

Another embodiment of the invention provides a protective barrier in the form of a brief. This embodiment of the invention is formed from an elongated, planar membrane of durable film material having, when placed flat, a horizontal axis and outlined configuration that is symmetrical about the axis. The outlining configuration has a vertical extension portion that extends upwardly to shield the wearer's genitalia and, that extends downwardly and rearwardly to shield the wearer's anus. There are disclosed herein four variations of this embodiment of the invention, including a simple brief, a dual brief, a cinch adjustable brief, and an hour glass brief. All four briefs are secured to the wearer by various means, discussed below.

Figure 2:
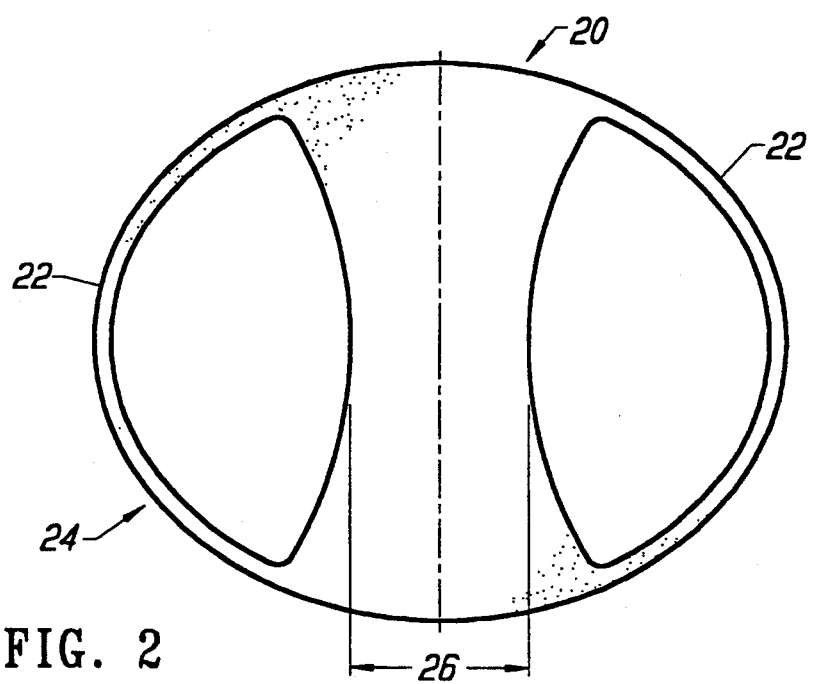
FIG. 2 is a top plan view of a simple brief according to another embodiment of the invention.

FIG. 2 is a top plan view of a simple brief according to one embodiment of the invention. The simple brief 20 is an oval shaped device with an hour glass center. It has openings between the center and perimeter which form one set of straps 22 which fit around thighs of the wearer and hug the thighs. One advantage of the simple brief design is that it offers protection for those having large body sizes. Unlike prior art briefs, the simple brief invention is formed of a material that clings to the wearer's skin and therefore conforms to the contour of the wearer's body, providing a natural sensation to the wearer's partner. The preferred embodiment of the simple brief has a 23×14-inch oval exterior 24 and a 5-inch midcenter 26. It is expected that the simple brief may be provided in other sizes as desired.

FIG. 3 is a top plan view of a dual brief according to another embodiment of the invention. The dual brief 30 is constructed of a material similar to that of the simple brief. The dual brief also includes two sets of straps 32,34 for different thigh sizes. One advantage of the dual brief is that it can fit wide and thick thighs with less concern of slippage.

The dual strap sets 32,34 provide the wearer the option of using either of the two strap sets depending upon the wearer's thigh thickness. The dual brief uses the cohesive attraction of the brief material to the wearer's skin, and center portion curvature 36 to secure the brief around the wearer's inner thigh. Wearers having thin thighs may use the interior set of straps 32 when wearing the brief; and wearers having wider thighs may use the exterior set of straps 34 when wearing the brief. This embodiment of the invention provides the wearer protection against exchanging body fluids with a partner, while lessening the need of the wearer to tie excess strap material into a knot to assure a snug fit. The preferred embodiment of the dual brief is a 23×14-inch oval having a 5-inch midcenter. It is expected that the dual brief may be provided in other sizes as desired, and may also be provided with more than two sets of straps to accommodate a wider variety of body sizes.

FIG. 4 is a top view plan of a cinch adjustable brief according to another embodiment of the invention. The cinch adjustable brief 40 is made from a material that is similar to that of the simple brief. The cinch adjustable brief also includes cinch locks 42 on a single set of straps 44 that allow for thigh size variations among different wearer's. The cinch adjustable brief provides the wearer with a tailored thigh fit that is not offered by previous briefs. The preferred embodiment of the cinch brief is a 23×14-inch oval having a 5-inch midcenter. It is expected that the cinch brief may be provided in other sizes as desired, and may also be provided with one set of cinches instead of the two sets of cinches shown in the figure.

The cinch adjustable brief uses a cinch lock (indicated in detail by numeric designator 46 on FIG. 4) to set the desired tightness of the leg straps. When the cinch lock 42 is in place, it slides along the leg straps 44 to secure strap around the thigh. The cinch brief includes one lock for each strap set, or two locks per brief. The cinch lock in the preferred embodiment of the invention is a round flat plastic disc with two slots 47,48 on opposing sides of the disc. Each strap is woven through the first slot 47 over the midsection of the disc and back through the second slot 48.

Figure 5:
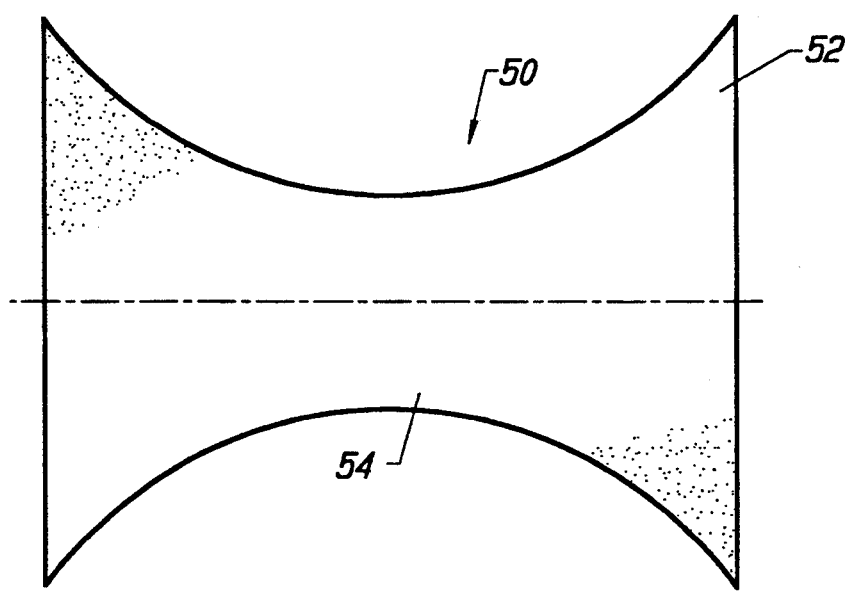
FIG. 5 is a top plan view of an hour glass brief according to another embodiment of the invention.

FIG. 5 is a top plan view of an hour glass brief according to another embodiment of the invention. The hour glass brief is made of a material that is similar to that of the simple brief. However, the hour glass brief is a strapless limitless thigh protective garment. One advantage the hour glass brief is that it fits most variations in body size. That is, the hour glass brief can be used by all wearer's regardless of thigh sizes because the brief is strapless. The hour glass brief 50 is secured to the wearer by cohesive attraction between the brief and the wearer's skin. Thus, to secure the hour glass brief in place, the wearer places a rear portion 52 of the brief into contact with her behind. The mid-portion 54 of the brief is adhered to area about the wearer's vulva by the action of the wearer's body fluids upon the material of the brief. The brief curvature rests along the wearer's inner thigh. The preferred embodiment of the hour glass brief has a 10-inch exterior width, a 5-inch center, and a length of 14 inches. It is expected that the hour glass brief may be provided in other sizes as desired.

The preferred material for fabricating both the mask and the brief embodiments of the invention may include either plastic or latex, having a thickness from 0.0125–0.004 inches and having a density that is less than 25-nm. The material should be resilient, strong, and it should provide a barrier to viruses. The material may be formed as shown in the figures by cutting, stamping, or other known means.

An important aspect of the invention is the ability of the mask or brief to cling to the wearer's skin and conform the contours and profile of the wearer, such that the mask or brief, when worn, is not so different from the wearer's skin as to detract from the partner's enjoyment. The cling of the material is perhaps even more important in that it secures the mask or brief in place against slippage and thereby prevents dislodging of the garment, which could result in an undesired transfer of fluids between the partners.

Although the invention is described herein with reference to the preferred embodiment, one skilled in the art will readily appreciate that other applications may be substituted for those set forth herein without departing from the spirit and scope of the present invention. Accordingly, the invention should only be limited by the Claims included below.

I claim:

1. A disposable brief for preventing the exchange of body fluids between partners during sexual activity, comprising:

a protective barrier formed of an elongated planar virus impermeable membrane, wherein said membrane is formed of a material chosen from among latex and plastic, said material having a thickness of about 0.00125 to 0.004 inches and a density of less than 25 nm, said protective barrier having a horizontal axis and an outlined configuration symmetrically formed about said axis which defines the shape of said brief, said membrane exhibiting plastic cohesive attraction to a brief wearer's skin to secure the brief in place, and such that said brief is conformable to the contours of the wearer's body; and at least one set of thigh straps integrated into the brief to secure the brief in place, and to accommodate any of various sized wearers.

2. The brief of claim 1, further comprising:

at least one set of adjustable fasteners for securing the brief in place and thereby allow the brief to accommodate any of various sized wearers.

3. The brief of claim 1, wherein said outlined configuration provides a brief having an hour glass shape.

* * * * *